(12) United States Patent
Shioda et al.

(10) Patent No.: US 8,053,731 B2
(45) Date of Patent: Nov. 8, 2011

(54) IMAGE FORMING APPARATUS AND IMAGE FORMING METHOD

(75) Inventors: Michinori Shioda, Yokohama (JP); Toshihiko Ouchi, Sagamihara (JP); Ryota Sekiguchi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 894 days.

(21) Appl. No.: 12/057,951

(22) Filed: Mar. 28, 2008

(65) Prior Publication Data

US 2008/0243410 A1    Oct. 2, 2008

(30) Foreign Application Priority Data

Apr. 2, 2007    (JP) ................. 2007-095950

(51) Int. Cl.
*G01J 5/02* (2006.01)
(52) U.S. Cl. .................. 250/341.1
(58) Field of Classification Search .......... 250/330–335, 250/336.1, 336.2, 338.1–338.5, 339.01–339.15, 250/340, 341.1–341.8
See application file for complete search history.

(56) References Cited

U.S. PATENT DOCUMENTS

| | | | |
|---|---|---|---|
| 5,623,145 A | 4/1997 | Nuss | |
| 5,710,430 A | 1/1998 | Nuss | |
| 5,867,213 A | 2/1999 | Ouchi | ............ 348/208 |
| 6,815,683 B2 | 11/2004 | Federici et al. | |
| 2004/0065831 A1 | 4/2004 | Federici et al. | |
| 2005/0061977 A1* | 3/2005 | Carr | ............ 250/338.1 |

FOREIGN PATENT DOCUMENTS

| | | |
|---|---|---|
| JP | 8-320254 | 12/1996 |
| JP | 2006-508333 | 3/2006 |

* cited by examiner

*Primary Examiner* — Kiho Kim
(74) *Attorney, Agent, or Firm* — Fitzpatrick, Cella, Harper & Scinto

(57) ABSTRACT

Provided are an image forming apparatus and an image forming method which are capable of obtaining an image of a measured object using a relatively simple structure in a short time. In the image forming apparatus, an electromagnetic wave generated by an electromagnetic wave generator is emitted to the measured object through a spatial modulation unit for spatially modulating a signal intensity. An electromagnetic wave that has passed through the measured object is measured by an electromagnetic wave detecting unit. A measurement signal is processed by a signal processing section based on a reference signal synchronized with the signal intensity modulated by the spatial modulation unit. The image is formed by an image acquisition section.

9 Claims, 6 Drawing Sheets

IMAGE FORMING APPARATUS AND IMAGE FORMING METHOD

BACKGROUND OF THE INVENTION

1. Field of the Invention

The present invention relates to an image forming apparatus and an image forming method, and more particularly, to an image forming apparatus and an image forming method which are used to generate an image of an object with an electromagnetic wave including at least one frequency of a frequency region from 30 GHz to 30 THz (referred to as a terahertz (THz) wave in this specification).

2. Description of the Related Art

Up to now, a method of generating a terahertz image of an object based on a signal of a terahertz wave has been proposed (see Japanese Patent Application Laid-Open No. H08-320254). According to the method, the terahertz wave is focused on a specific region of the object. The object is moved such that the focus point passes through each of multiple spatially separated regions of the object. Respective transmitted signals propagating through the spatially separated points of the object are collected. The signals are processed to generate the image of the object.

In the case of imaging using the method, in order to increase the intensity of the terahertz wave to improve an S/N ratio, the terahertz wave is focused on a single point of the object. However, when the terahertz wave is focused on the single point, it is necessary to scan all the regions of the object with a point beam, so the imaging takes a long period of time.

Therefore, Japanese Patent Application Laid-Open No. H08-320254 describes a method involving irradiating the entire object with a terahertz beam and focusing the beam that has passed therethrough on a focal plane THz detector array by a lens system to perform imaging at once. However, the focal plane THz detector array is a two-dimensional array of THz dipole antennas, so a lock-in amplifier is required for each element to perform the imaging. Because the lock-in amplifier is a device which requires a space, when as many lock-in amplifiers as the number of elements used for the focal plane THz detector array are prepared, an apparatus becomes very large in size. Thus, methods of easily performing imaging using a small-size apparatus in a short time have been expected.

A method using, as a terahertz wave detector, a pyroelectric sensor array which operates at normal temperature and has a small size has been studied as one of the methods of easily performing imaging using a small-size apparatus in a short time. The pyroelectric sensor array is sensitive to infrared light, but the sensitivity to the terahertz wave is not sufficient and the response characteristic is insufficient, so long-time averaging is performed to increase the S/N ratio. Therefore, according to the method, it is difficult to perform short-time imaging.

An imaging system and an imaging method which are used for imaging with the terahertz wave have been proposed (see Japanese Patent Application Laid-Open No. 2006-508333). In the imaging method, an interference pattern is generated using multiple terahertz wave sources and a signal thereof is detected by an interferometer array including multiple spaced detectors. A Fourier component on the Fourier-transform plane is produced based on the detected signal and then inverse-Fourier-transformed for image reconstruction. However, the method provides a spatial THz imaging technique capable of simultaneously detecting THz waves from the multiple THz wave sources within a wide "field of view", so the multiple THz wave sources are necessary.

SUMMARY OF THE INVENTION

In view of the above-mentioned circumstances, a relatively small-size image forming apparatus and an image forming method which are capable of performing terahertz imaging in a short time have been desired.

The present invention is directed to an image forming apparatus, comprising: an electromagnetic wave generator; an electromagnetic wave detecting unit; a spatial modulation unit for applying a spatial signal intensity modulation which includes at least one period component to an electromagnetic wave output from the electromagnetic wave generator; a signal processing section for inputting an electromagnetic wave spatially modulated by the spatial modulation unit into the electromagnetic wave detecting unit through an object to be measured to extract a signal of a component synchronized with the spatial signal intensity modulation applied by the spatial modulation unit from a measurement signal detected by the electromagnetic wave detecting unit; and an image acquisition section for image-processing a signal from the signal processing section to obtain an image of the object to be measured.

The electromagnetic wave detecting unit can comprise a two-dimensional electromagnetic wave detector array.

The spatial modulation unit can apply to the electromagnetic wave which reaches the electromagnetic wave detecting unit the spatial signal intensity modulation which has a period equal to or shorter than a wavelength of the electromagnetic wave output from the electromagnetic wave generator. The spatial modulation unit can have a constitution which makes a dielectric constant spatially vary at the period equal to or shorter than the wavelength of the electromagnetic wave emitted from the electromagnetic wave generator. The spatial modulation unit can be comprised of a material the dielectric constant of which varies according to an applied voltage; and the dielectric constant spatially varies at the period equal to or shorter than the wavelength of the electromagnetic wave by controlling the applied voltage at an interval equal to or shorter than the wavelength of the electromagnetic wave. The spatial signal intensity modulation to be applied can consist of the modulations regarding two directions.

The signal processing section can prepare in advance a spatial reference signal having a period equal to the period of the spatial signal intensity modulation applied to the electromagnetic wave which reaches the electromagnetic wave detecting unit is spatially modulated by the spatial modulation unit, and can carry out a spatial synchronous detection using the measurement signal from the electromagnetic wave detecting unit and the spatial reference signal to extract from the measurement signal only a signal of a component corresponding to the period equal to the period of the spatial signal intensity modulation applied by the spatial modulation unit.

The electromagnetic wave can comprise an electromagnetic wave including at least one frequency of a frequency region from 30 GHz to 30 THz.

The present invention is directed to an image forming method, comprising the steps of: applying to an electromagnetic wave a spatial signal intensity modulation which includes at least one period component equal to or smaller than a wavelength of the electromagnetic wave to apply the spatial signal intensity modulation to an electromagnetic wave which reaches from an object to be measured which is to be irradiated with the electromagnetic wave to an electromagnetic wave detecting unit; carrying out a spatial synchronous detection using a measurement signal derived from the electromagnetic wave which reaches the electromagnetic wave detecting unit and a spatial reference signal previously prepared and synchronized with the spatial signal intensity modulation to extract a signal of a component synchronized with the spatial signal intensity modulation from the measurement signal; and image-processing the extracted signal to obtain an image of the object to be measured.

According to the present invention, an image forming apparatus includes an electromagnetic wave generator, an electromagnetic wave detecting unit, a spatial modulation unit for spatially modulating a signal intensity of an electromagnetic wave which reaches the electromagnetic wave detecting unit to include at least one period component, a signal processing section, and an image acquisition section. In the image forming apparatus, the signal processing section extracts a signal of a component synchronized with the signal intensity modulated by the spatial modulation unit from a measurement signal detected by the electromagnetic wave detecting unit when the electromagnetic wave emitted from the electromagnetic wave generator passes though a measured object and the spatial modulation unit and reaches the electromagnetic wave detecting unit. The image acquisition section image-processes a signal from the signal processing section to obtain an image of the measured object.

Further, in view of the above object, an image forming method according to the present invention includes: spatially modulating a signal intensity of an electromagnetic wave to include a component of at least one period equal to or shorter than a wavelength of the electromagnetic wave, to spatially modulate a signal intensity of an electromagnetic wave which passes through a measured object and reaches an electromagnetic wave detecting unit; performing spatial synchronous detection based on a measurement signal obtained from the electromagnetic wave which reaches the electromagnetic wave detecting unit and a spatial reference signal which has the same period as that of the modulated intensity and prepared in advance, to extract, from the measurement signal, a signal of a component synchronized with the modulated intensity; and image-processing the extracted signal to obtain an image of the measured object.

According to the present invention, spatial lock-in detection or heterodyne detection can be employed. Even when the sensitivity of the detecting unit to the electromagnetic wave is not sufficient, the image of the measured object can be obtained in a short time using a relatively simple structure. The electromagnetic wave having any frequency can be used in principle. In particular, when a terahertz wave for which a high-sensitive detector and a high-power generator are easily obtained is used, the present invention has a significant effect.

Further features of the present invention will become apparent from the following description of exemplary embodiments with reference to the attached drawings.

DESCRIPTION OF THE EMBODIMENTS

Figure 1:
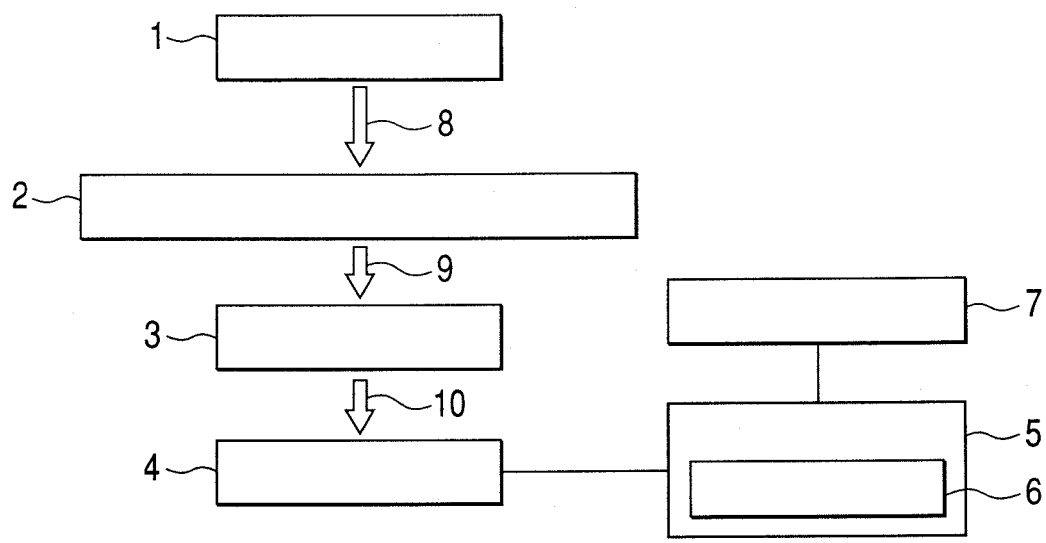
FIG. 1 is a schematic diagram illustrating a fundamental structure of an image forming apparatus according to Embodiment 1 of the present invention.

Preferred embodiments of the present invention will now be described in detail in accordance with the accompanying drawings As illustrated in FIG. 1, an image forming apparatus according to the present invention includes an electromagnetic wave generator 1 and an electromagnetic wave detector array 4 serving as an electromagnetic wave detecting unit.

The image forming apparatus further includes a spatial modulation unit 2 for spatially modulating a signal intensity of an electromagnetic wave (emitted electromagnetic wave 8) output from the electromagnetic wave generator 1 to include at least one period component.

The image forming apparatus further includes a signal processing section 5. When the electromagnetic wave whose signal intensity is spatially modulated by the spatial modulation unit is input to the electromagnetic wave detecting unit through a measured object 3, the signal processing section 5 extracts a signal of a frequency component synchronized with the signal intensity modulated by the spatial modulation unit, from a measurement signal detected by the electromagnetic wave detecting unit. The image forming apparatus further includes an image acquisition section 7 for image-processing the signal from the signal processing section 5 to acquire an image of the measured object.

The feature of the image forming apparatus is to have the structure described above. Hereinafter, the present invention will be described in more detail with reference to specific embodiments.

Embodiment 1

FIG. 1 is a schematic structural explanatory diagram illustrating Embodiment 1 of the present invention. In this embodiment, as illustrated in FIG. 1, the sample (measured object) 3 is irradiated with the emitted electromagnetic wave 8 from the electromagnetic wave generator 1 through the spatial modulation unit 2 for spatially modulating the signal intensity of the electromagnetic wave. An electromagnetic wave 10 that has passed through the sample 3 is detected by the electromagnetic wave detector array 4 serving as the electromagnetic wave detecting unit. The signal detected by the electromagnetic wave detector array 4 is processed by the signal processing section 5 including a reference signal generating section 6 and image-processed by the image acquisition section 7 to display the image of the sample 3 on a display (not shown).

Figure 2A:
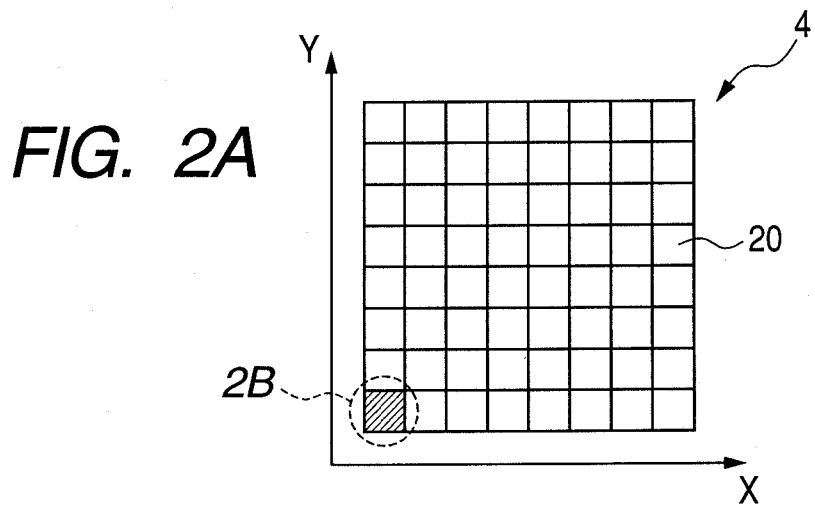
FIGS. 2A, 2B, and 2C are explanatory diagrams illustrating an electromagnetic wave detector array and a measurement signal.
Figure 2B:
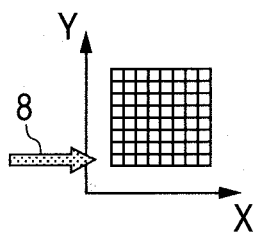

To be specific, a terahertz wave including at least one frequency of a frequency region from 30 GHz to 30 THz is irradiated as the emitted electromagnetic wave 8. For example, an electromagnetic wave whose frequency is 1 THz can be emitted to the sample 3. The terahertz wave passes through a material such as a paper or a plastic because the terahertz wave has the property of passing through, for example, a non-polar material. When the sample 3 is such a material transmitting the terahertz wave, the electromagnetic wave 10 that has passed through the sample 3 can be detected by the electromagnetic wave detector array 4. As illustrated in FIGS. 2A and 2B, the electromagnetic wave detector array 4 is, for example, a two-dimensional array of pyroelectric elements (each having 3 μm×3 μm).

The spatial modulation unit 2 is used to spatially modulate the signal intensity of the emitted electromagnetic wave 8 from the electromagnetic wave generator 1 at a period equal to or shorter than a wavelength thereof to detect the modulated electromagnetic wave by the electromagnetic wave detector array 4. In other words, it is undesirable to set each pixel size of the electromagnetic wave detector array 4 to a value equal to or shorter than the wavelength of the emitted electromagnetic wave 8 in view of diffraction. A modulation frequency in the case where the signal intensity is spatially modulated by the spatial modulation unit 2 is a spatial frequency corresponding to a period smaller than the pixel size of the electromagnetic wave detector array 4. When the electromagnetic wave whose frequency is 1 THz is used as the emitted electromagnetic wave 8, the wavelength thereof is 300 μm. Therefore, the pixel can be assumed as, for example, a region of 300 μm×300 μm, which is equal to the wavelength. Thus, the spatial modulation unit 2 is designed so as to spatially modulate the signal intensity at a period equal to or smaller than 300 μm. In order to suitably detect a very small signal buried in noise by signal processing described later, it is desirable to spatially modulate the signal intensity of the electromagnetic wave at the period equal to or shorter than the wavelength thereof.

Figure 2C:
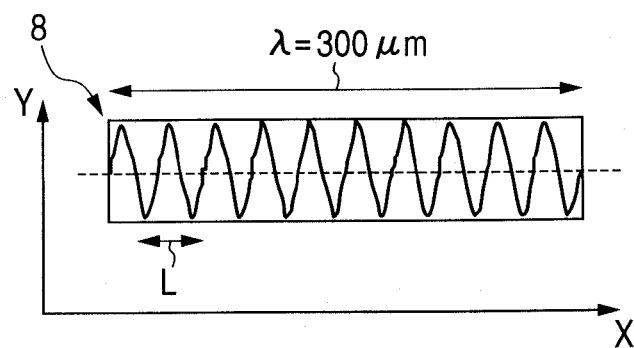

FIGS. 2A, 2B, and 2C are explanatory diagrams illustrating the electromagnetic wave detector array 4 and the measurement signal. FIG. 2A is a schematic front diagram illustrating a front of the electromagnetic wave detector array 4 and illustrates a state in which pixels 20 are two-dimensionally arranged in an X-direction and a Y-direction. As illustrated in FIG. 2B, each of the pixels 20 includes elements two-dimensionally arranged in the X-direction and the Y-direction. When such a two-dimensional array is employed, imaging described later can be performed in a short time.

FIG. 2C illustrates an example of signals detected by the respective elements of the electromagnetic wave detector array 4 in the case where the signal intensity of the emitted electromagnetic wave 8 from the electromagnetic wave generator 1 is spatially modulated by the spatial modulation unit 2 at the period equal to or shorter than the wavelength thereof to detect the modulated electromagnetic wave by the electromagnetic wave detector array 4. For simple description, signals detected by an element line (X-direction) located in the lowermost part of FIG. 2B are illustrated. The abscissa indicates a position coordinate (X-direction) and the ordinate indicates a signal intensity. As described earlier, the pixel size in each of the X-direction and the Y-direction is set to 300 μm equal to the wavelength of the electromagnetic wave whose frequency is 1 THz. The signals at this time are signals detected in the case where a spatially modulated electromagnetic wave 9 is emitted to the entire surface of the electromagnetic wave detector array 4 while the sample 3 is not located.

Assume that the wavelength of the emitted electromagnetic wave 8 from the electromagnetic wave generator 1 is expressed by λ, a length (period) for which the spatial signal intensity modulation is performed is expressed by L, and a pixel length in each of the X-direction and the Y-direction is equal to the wavelength λ. In this case, the number of periods (M) per pixel length in each direction is expressed by "M=λ/L". When the same emitted electromagnetic wave 8 is generated, the wavelength thereof is the same. Therefore, the number of periods (M) occupying a space equal to the wavelength λ increases as the length L for which the spatial signal intensity modulation is performed becomes short. In FIG. 2C, λ=300 μm and L=30 μm, so the number of periods (M) per pixel corresponding to the length of the wavelength λ is 10.

Two examples of a method of realizing the spatial modulation unit 2 include a method of realizing mechanical modulation and a method of realizing electrical modulation. In the mechanical method, the spatial modulation unit 2 to be used is constructed so as to have a size equal to or shorter than the wavelength of the emitted electromagnetic wave 8 from the electromagnetic wave generator 1 to periodically change a dielectric constant (or refractive index). For example, a grating is preferably made of metal, a fiber polymer material, or polymer silicon. In this embodiment, for example, an interval (period) of the grating is set to 30 μm.

In the electrical method, a material whose dielectric constant is changed according to an applied voltage is used. The applied voltage is controlled at an interval (for example, the order of approximately 100 nm in length) equal to or shorter than the wavelength of the electromagnetic wave to periodically adjust the spatial signal intensity of the emitted electromagnetic wave 8 at the period equal to or shorter than the wavelength thereof. Unlike the mechanical method, the electrical method has an advantage that a length of the spatial period is arbitrarily and flexibly adjusted by controlling the applied voltage. When the length is adjusted, a reference signal 12 described later is prepared again based on the adjusted length by the reference signal generating section 6 using a computer (not shown) and then stored in the signal processing section 5.

Figure 3:
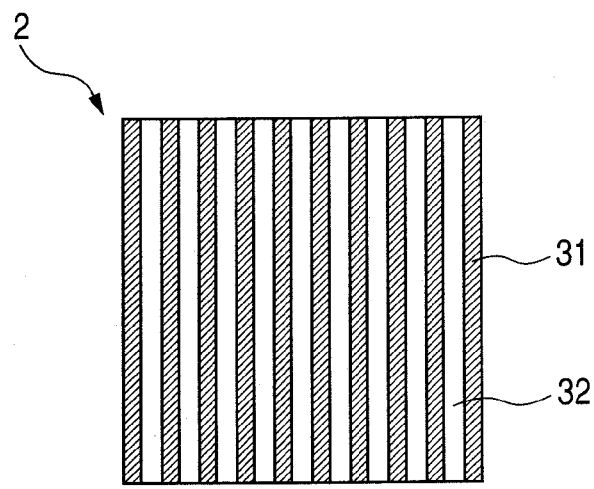
FIG. 3 is a front view (schematic view) illustrating a grating made of silicon, which is used in Embodiment 1 of the present invention and serves as a spatial modulation unit.

In this embodiment, for example, silicon is used to realize the spatial modulation unit 2 according to the mechanical method. An example of the spatial modulation unit 2 according to the mechanical method is illustrated in FIG. 3. The spatial modulation unit (grating) 2 includes silicon portions 31 arranged at a pitch of 30 μm in the X-direction. A refractive index and a width of each of the silicon portions 31 are 3.4 and 15 μm, respectively. Each space 32 between adjacent silicon portions is filled with air whose refractive index is 1.0. In this case, the direction in which the signal intensity is modulated is a single direction, that is, the X-direction.

Figure 4:
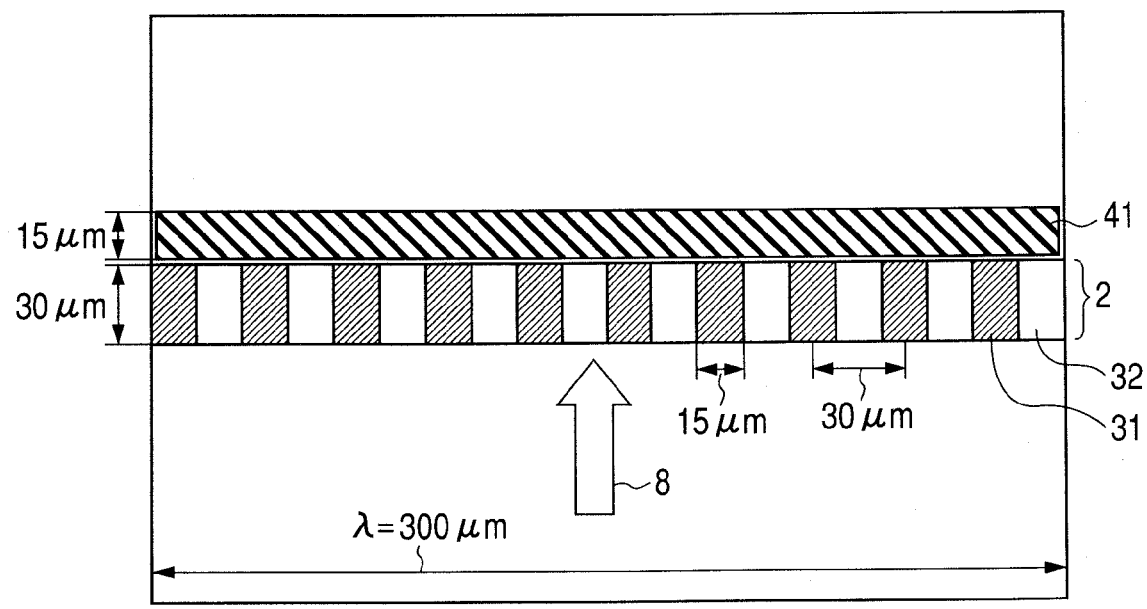
FIG. 4 illustrates a state in which an electromagnetic wave is emitted to the spatial modulation unit.

FIG. 4 is a cross sectional view illustrating a state in which the terahertz wave is being emitted to the spatial modulation unit 2 of FIG. 3. The grating 2 which is made of silicon and corresponds to a pixel (300 μm in length) is illustrated in the central area of FIG. 4. Each of the silicon portions has a refractive index of 3.4, a lateral width of 15 μm, a depth (thickness) of 30 μm. The silicon portions are arranged at a pitch of 30 μm. The space between adjacent silicon portions is filled with air (1.0 in refractive index). As illustrated in FIG. 4, when the terahertz wave 8 whose frequency is 1 THz is emitted from the lower side to the grating 2 made of silicon in the perpendicular direction, the signal intensity of the emitted electromagnetic wave 8 is modulated in a region close to the grating 2. The region in which the emitted electromagnetic wave 8 is modulated (region close to the grating 2) corresponds to a portion 41 indicated by diagonal lines of FIG. 4 and has a depth (thickness) of approximately 15 μm equal to a size (width) of an aperture (portion filled with air). Therefore, when the sample 3 and the elements of the electromagnetic wave detector array 4 are disposed in the region based on the position relationship of FIG. 1, the spatially modulated signal that has passed through the sample 3 can be detected.

Only the elements of the electromagnetic wave detector array 4 may be disposed in the region and the sample 3 may be disposed between the spatial modulation unit 2 and the electromagnetic wave generator 1. In this case, it is necessary to construct an optical system so as to image the electromagnetic wave that has passed through the sample 3 onto the electromagnetic wave detector array 4. In this embodiment, as illustrated in FIG. 1, the method is employed in which the sample 3 is located immediately after the spatial modulation unit 2.

Figure 5A:
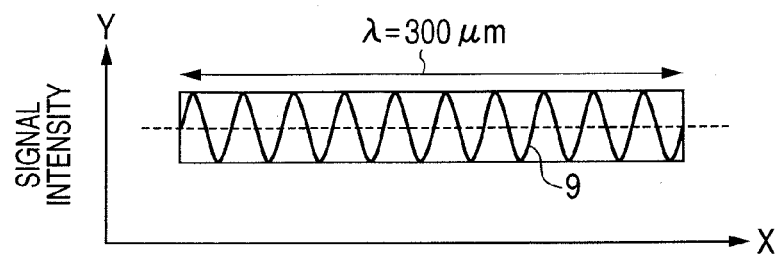
FIGS. 5A, 5B, and 5C are explanatory diagrams illustrating a modulation signal, a reference signal, and a measurement signal in an X-direction of a pixel
Figure 5B:
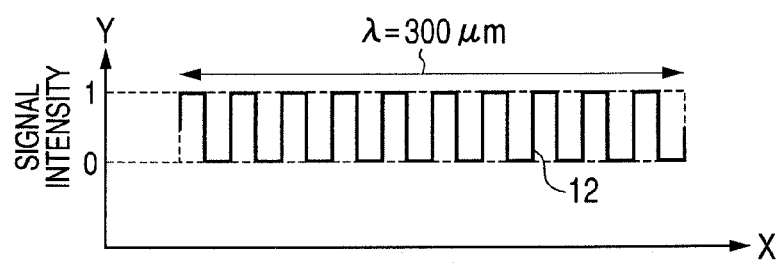
Figure 5C:
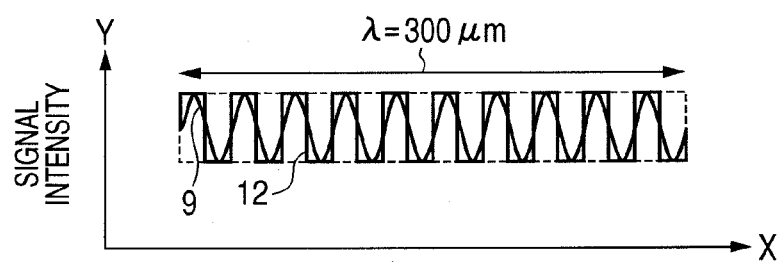

The signal detected by each of the elements of the electromagnetic wave detector array 4 is sent to the signal processing section 5. In order to realize spatial lock-in detection, the signal processing section 5 requires the spatial reference signal 12. Therefore, the reference signal 12 is prepared in advance in the signal processing section 5 by the reference signal generating section 6 using the computer. The spatial reference signal 12 is required to be a signal synchronized with the modulation signal (spatially modulated electromagnetic wave) 9 obtained by the spatial modulation unit 2. For example, when the modulation signal 9 as illustrated in FIG. 5A is obtained by the spatial modulation unit 2, the spatial reference signal 12 has, for example, the same period illustrated in FIG. 5B. Note that the signal illustrated in FIG. 5A indicates a signal in the case where the emitted electromagnetic wave 8 irradiates the entire surface while the sample 3 is not set. The signal intensity is in an arbitrary unit. FIG. 5C illustrates a state in which the modulation signal 9 and the reference signal 12 are superimposed on each other in the same position in order to simplify a position relationship (X-direction) between the modulation signal 9 and the reference signal 12.

Figure 5D:
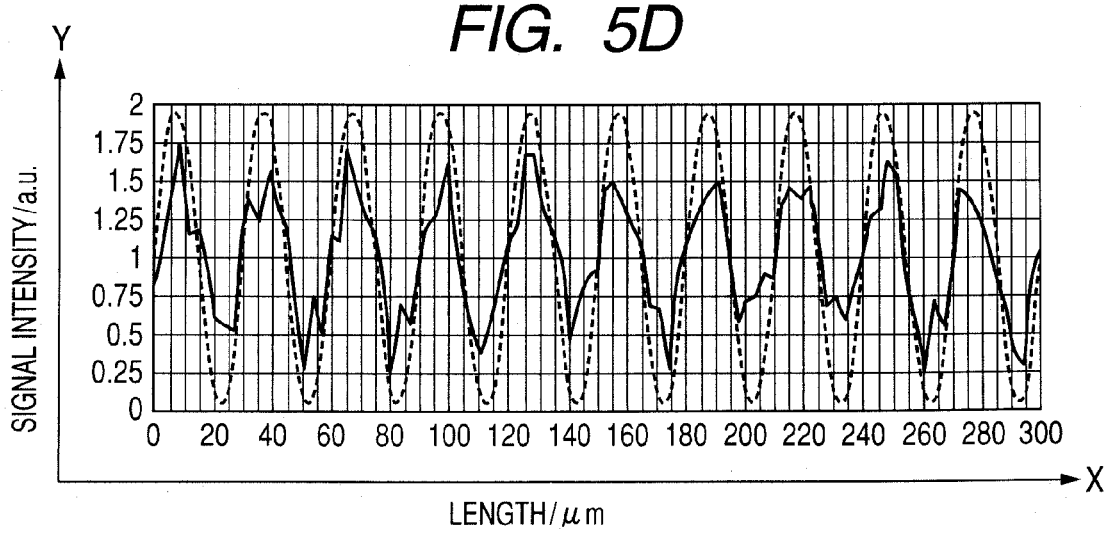
FIG. 5D is an explanatory diagram illustrating a modulation signal, a reference signal, and a measurement signal in the X-direction of the pixel.

In an actual case, there is the sample 3. Therefore, a measurement signal in the case where the electromagnetic wave that has passed through the sample 3 is detected by the electromagnetic wave detector array 4 is smaller in signal intensity than the modulation signal 9 of FIG. 5A. An actual measurement signal to be detected is mixed with noise (for example, white noise changed for each element in each pixel) generated from the electromagnetic wave detector array 4. Therefore, the measurement signal is different from the signal illustrated in FIG. 5A. FIG. 5D illustrates an example of the measurement signal which is indicated by a solid line. For comparison, FIG. 5D also illustrates the modulation signal 9 indicated by a broken line.

Next, a method of performing the spatial lock-in detection (or heterodyne detection) will be described.

Figure 6:
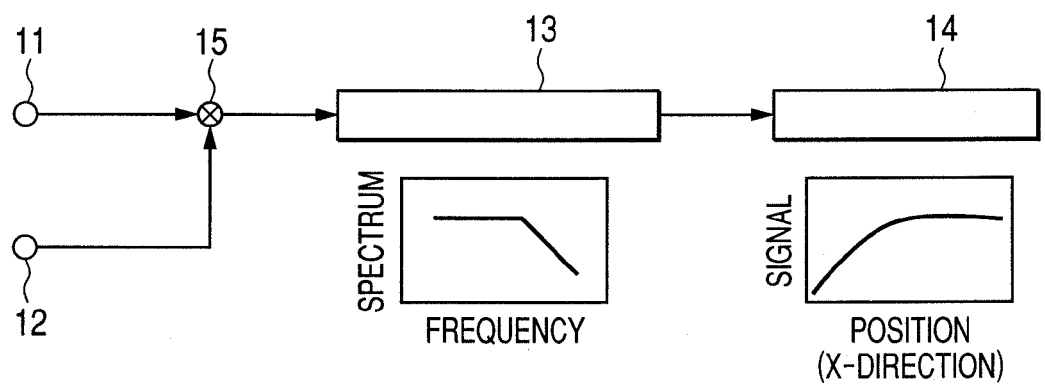
FIG. 6 is an explanatory diagram illustrating a principle for reducing noise from the measurement signal and the reference signal.

For easy understanding, assume that a length unit (μm) in the abscissa of FIG. 5D is replaced by a time unit (seconds (s)). Then, the description of the principle of the lock-in detection in a time domain can be used here. As illustrated in FIG. 6, when a measurement signal 11 from the electromagnetic wave detector array 4 is multiplied by a multiplier 15 by the reference signal 12 prepared in advance, of various signals included in the measurement signal 11, only a component equal in frequency to the reference signal 12 becomes a direct current component, so the component can pass through a low-pass filter 13. When the cutoff frequency of the low-pass filter 13 is suitably selected, the signal that has passed through the low-pass filter 13 (filter output 14) converges to a predetermined value as the position coordinates in the X-direction are successively read. The converged value is assumed as a value of all the elements in the read X-direction, that is, a signal of a pixel.

Figure 7A:
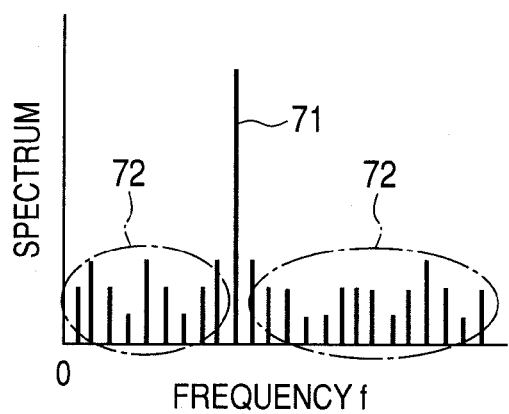
FIGS. 7A and 7B are explanatory diagrams illustrating the principle of FIG. 6 in a frequency region.
Figure 7B:
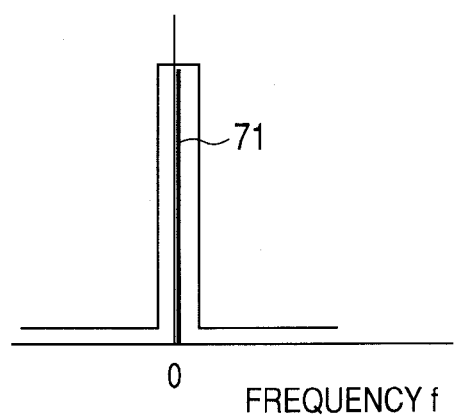

This will be described using an FFT in a frequency domain. FIG. 7A schematically illustrates spectrums of the measurement signal 11 (solid line in FIG. 5D) which is obtained by the FFT. It is apparent that there is a spectrum of the modulation signal at a modulation frequency 71 and there are spectrums of noises 72 which are equal to each other at frequencies other than the modulation frequency 71. The operation in which the modulation signal is demodulated and filtered by the low-pass filter (LPF) 13 corresponds to an operation in which, as illustrated in FIG. 7B, the modulation frequency 71 of the modulation signal is shifted to a frequency of zero (0) to cut signals other than the direct current component, thereby reducing the spectrums of the noises.

When the operation described above is performed for each pixel, the noises can be reduced from the measurement signal 11. Digital processing of the signal processing section 5 may be performed by parallel processing using multiple CPUs. A part of the digital processing may be performed by an analog circuit during parallel processing. Therefore, the time required for imaging can be shortened.

As described above, when the spatial signal intensity modulation is performed at the period equal to or shorter than the wavelength of the electromagnetic wave and the measurement signal from the electromagnetic wave detector array 4 is spatially synchronously detected, a very small signal buried in noise can be detected with high precision.

The spatial lock-in detection method performed by the signal processing section 5 described above is summarized as follows. The signal intensity of the electromagnetic wave which will reach the electromagnetic wave detecting unit 4 is spatially modulated by the spatial modulation unit 2 at a predetermined period. The spatial reference signal 12 having a period equal to the predetermined period is prepared in advance in the signal processing section 5. The spatial synchronous detection is performed based on the measurement signal 11 from the electromagnetic wave detecting unit 4 and the spatial reference signal 12 to extract, from the reference signal 11, a signal of a frequency component corresponding to the period equal to the predetermined period at which the signal intensity is modulated by the spatial modulation unit 2. When the signal is extracted from the measurement signal 11, it is also desirable to extract only the signal of the frequency component corresponding to the period equal to the predetermined period at which the signal intensity is modulated by the spatial modulation unit 2.

That is, it is suitable to selectively extract a signal of a component with the same period as of the signal intensity modulation applied by the spatial modulation unit 2. However, where the low-pass filter 13 in FIG. 6 is not ideal, there is a possibility that only the signal of a component with the same period as of the signal intensity modulation applied by the spatial modulation unit 2 cannot be extracted but some noises surrounding the modulation frequency of FIG. 7A are contained. But, even in such a case, the amount of the noise is sufficiently smaller than that of the signal corresponding to the modulation frequency so that it is possible to make the image through the above image-treatment.

In order to form an image based on processed signals, the processed signals are arranged in a suitable order in the image acquisition section 7 to acquire an image. The image may be displayed without any processing. Because each of the signals is processed for each pixel, so there is the case where a seam between pixels becomes discontinuous. Therefore, if necessary, image processing using a smoothing filter is performed or image processing using a window function is performed, so image quality can be improved.

The image forming process can be described as the following image forming method. The signal intensity of the electromagnetic wave is spatially modulated at the predetermined period equal to or shorter than the wavelength thereof to spatially modulate the signal intensity of the electromagnetic wave which is emitted to the measured object 3 and reaches the electromagnetic wave detecting unit 4. The spatial synchronous detection is performed based on the measurement signal 11 obtained from the electromagnetic wave which reaches the electromagnetic wave detecting unit 4 and the spatial reference signal 12 which is prepared in advance and has the period equal to the predetermined period at which the signal intensity is spatially modulated. Therefore, the signal of the frequency component corresponding to the period equal to the predetermined period at which the signal intensity is spatially modulated is extracted from the measurement signal 11. The extracted signal is image-processed to obtain the image of the measured object 3. When the signal is extracted from the measurement signal 11, it is also desirable to extract only the signal of the frequency component corresponding to the period equal to the predetermined period at which the signal intensity is modulated by the spatial modulation unit 2.

According to this embodiment described above, it is unnecessary to focus the electromagnetic wave on a point to perform scanning with a point beam. Therefore, an image whose S/N ratio is high can be obtained in a short time by the relatively simple structure. Even when the detector is not sufficiently sensitive to the electromagnetic wave such as the terahertz wave, a desirable image can be easily obtained in a short time and a small-size apparatus capable of easily obtaining a terahertz wave image in a short time can be realized. Further, an apparatus capable of obtaining a terahertz wave image without requiring multiple THz wave sources can be realized.

Up to now, there is a method of performing lock-in detection using a mechanical chopper (in the method, for example, the spatial modulation unit 2 illustrated in FIG. 1 is replaced by the mechanical chopper). According to the method, for example, a current signal output from a terahertz pulse light detector is a very weak signal, so pump pulse light generated on an electromagnetic wave generation side is modulated using the mechanical chopper. A current signal detected on an electromagnetic wave detection side is converted into a voltage signal. Then, the lock-in detection is performed by a lock-in amplifier using a signal having a drive frequency of the mechanical chopper as a reference signal to measure a temporal change in electric field strength of the terahertz pulse light.

Unlike the method of modulating the intensity of the electromagnetic wave with time by the mechanical chopper, this embodiment is to spatially modulate the intensity of the electromagnetic wave by the spatial modulation unit 2. Therefore, the signal processing methods for the detection side are different from each other. That is, in this embodiment, the reference signal used to perform lock-in amplification by the lock-in amplifier is desirably prepared in advance and stored, corresponding to the spatial modulation frequency (period) of the spatial modulation unit 2 which is already determined. Even when multiple spatial modulation frequencies are used in the spatial modulation unit 2 as in the case of Embodiment 3 described later, it is desirable to prepare multiple reference signals having frequencies in advance corresponding to the spatial modulation frequencies and select a reference signal at the time of signal processing. In contrast to this, in the method using the mechanical chopper for modulating the intensity of the electromagnetic wave with time, it is necessary to prepare the reference signal for each time based on the frequency at which the mechanical chopper is driven. Therefore, the structure in this embodiment is relatively simpler than the case of the method using the mechanical chopper.

Embodiment 2

Embodiment 2 of the present invention will be described with reference to the attached drawings. The fundamental structure in this embodiment is identical to the structure of FIG. 1 which is described in Embodiment 1. The processings of the spatial modulation unit 2 and the signal processing section 5 in this embodiment are different from the processings in Embodiment 1.

Figure 8:
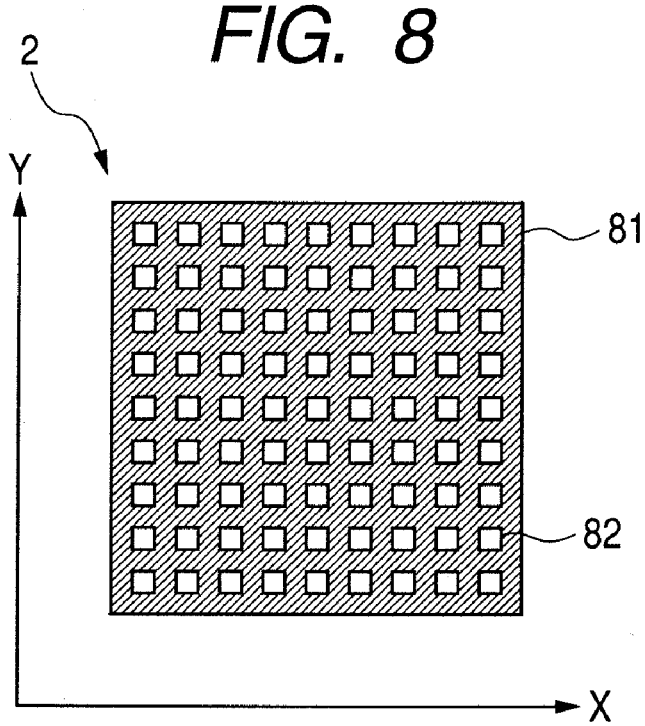
FIG. 8 is a front view (schematic view) illustrating a grating made of silicon, which is used in Embodiment 2 of the present invention and serves as a spatial modulation unit.

FIG. 8 illustrates the spatial modulation unit 2 used in this embodiment. As illustrated in FIG. 8, silicon portions 81 each of whose refractive index is 3.4 and width is 15 µm are arranged at a pitch of 30 µm in the longitudinal and lateral directions. Each space between adjacent silicon portions is filled with air 82 whose refractive index is 1.0. In Embodiment 1, the direction in which the signal intensity is modulated is the single direction, that is, the X-direction. In contrast, in this embodiment, two directions, that is, the X-direction and the Y-direction are set. Therefore, the signal intensity of the electromagnetic wave which reaches the electromagnetic wave detecting unit 4 is modulated in the two directions by the spatial modulation unit 2.

Figure 9:
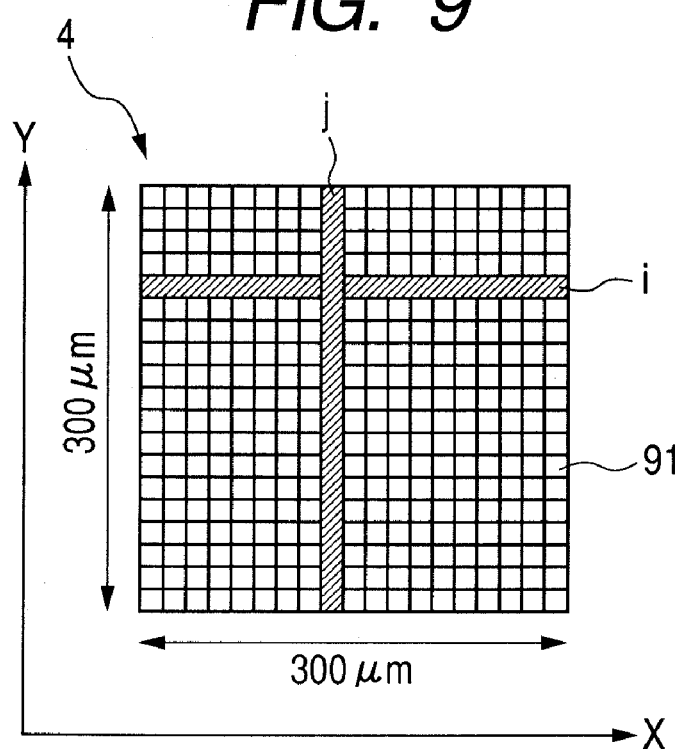
FIG. 9 is an enlarged view illustrating a pixel, which is an explanatory view illustrating an i-th row and j-th column of elements.

FIG. 9 is an enlarged view illustrating a pixel of the electromagnetic wave detector array 4. An i-th row and j-th column are indicated by black thick lines. Of the measurement signals 11, a measurement signal of the i-th row in the X-direction and a measurement signal of the j-th column in the Y-direction are used to reduce noise from each of the measurement signals by the method described in Embodiment 1. As a result, the filter outputs 14 from the low-pass filter 13 in each of the X-direction and the Y-direction are obtained. Reference numeral 91 denotes an element.

A value of the entire pixel is determined based on values of the two filter outputs 14. When the filter output 14 in the X-direction is expressed by $\alpha$ and the filter output 14 in the Y-direction is expressed by $\beta$, a value V of the entire pixel can be expressed by, for example, the following expression. Note that m and n indicate weighting parameters.

$$V=(m\alpha+n\beta)/(m+n)$$

When the above-mentioned operation is performed for each pixel, an image in which element information of the X-direction and the Y-direction are included and from which noise is reduced can be obtained. The others are identical to those in Embodiments 1.

Embodiment 3

Embodiment 3 of the present invention will be described. The fundamental structure in this embodiment is also identical to the structure of FIG. 1 which is described in Embodiment 1. This embodiment is different from Embodiment 1 in the point that the spatial modulation unit 2 is realized using the electrical method.

Figure 10A:
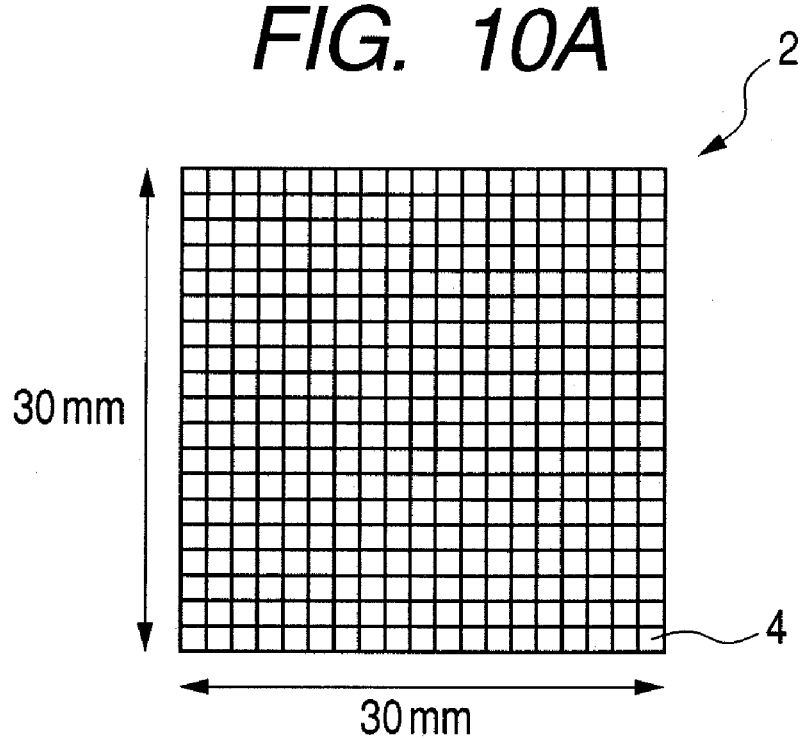
FIGS. 10A and 10B are explanatory views illustrating an electrical method of realizing a spatial modulation unit in Embodiment 3 of the present invention.
Figure 10B:
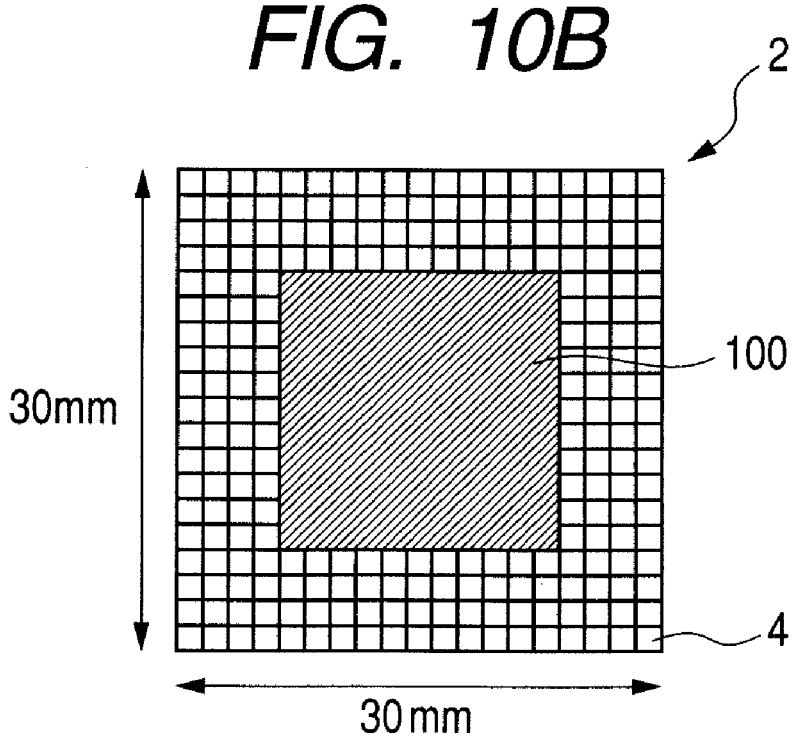

FIGS. 10A and 10B illustrate an example of the spatial modulation unit 2 which is electrically realized. A material whose dielectric constant is changed according to an applied voltage, for example, a liquid crystal material or a linear optical crystal material is used. The applied voltage to each portion is adjusted to be able to control a dielectric constant at each spatial position illustrated in FIGS. 10A and 10B in length unit of approximately 100 nm. Therefore, the spatial modulation manner can be changed. That is, the length L (see FIG. 2C) for the spatial signal intensity modulation can be changed.

For example, as illustrated in FIG. 10A, assume that a size of the spatial modulation unit 2 is 30 mm×30 mm. In this case, the length L for the spatial signal intensity modulation can be changed over the entire region every time the sample 3 is exchanged for another sample. For example, the spatial signal intensity modulation with L=300 μm can be changed to the spatial signal intensity modulation with L=30 μm by controlling the applied voltage.

As illustrated in FIG. 10B, even when the same sample 3 is used, the length L for the spatial signal intensity modulation of the spatial modulation unit 2 can be changed based on a spatial distribution of the sample 3. For example, the applied voltage is controlled to make L equal to 3 μm in a region 100 corresponding to the center portion of the sample 3. The applied voltage is controlled to make L equal to 30 μm in the other region. When the length L is changed, the multiple reference signals 12 are prepared corresponding to respective portions based on the changed length by the reference signal generating section 6 using a computer and then stored in the signal processing section 5. When the respective portions of the sample 3 are to be subjected to signal processing, a reference signal to be used is selected from the reference signals. The others are identical to those in Embodiments 1.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-095950, filed Apr. 2, 2007, which is hereby incorporated by reference herein in its entirety.

What is claimed is:

1. An image forming apparatus, comprising:
an electromagnetic wave generator;
an electromagnetic wave detecting unit;
a spatial modulation unit for applying a spatial signal intensity modulation which includes at least one period component to an electromagnetic wave output from the electromagnetic wave generator;
a signal processing section for inputting an electromagnetic wave spatially modulated by the spatial modulation unit into the electromagnetic wave detecting unit through an object to be measured to extract a signal of a component synchronized with the spatial signal intensity modulation applied by the spatial modulation unit from a measurement signal detected by the electromagnetic wave detecting unit; and
an image acquisition section for image-processing a signal from the signal processing section to obtain an image of the object to be measured.

2. An image forming apparatus according to claim 1, wherein the electromagnetic wave detecting unit comprises a two-dimensional electromagnetic wave detector array.

3. An image forming apparatus according to claim 1, wherein the spatial modulation unit applies to the electromagnetic wave which reaches the electromagnetic wave detecting unit the spatial signal intensity modulation which has a period equal to or shorter than a wavelength of the electromagnetic wave output from the electromagnetic wave generator.

4. An image forming apparatus according to claim 3, wherein the spatial modulation unit has a constitution which makes a dielectric constant spatially vary at the period equal to or shorter than the wavelength of the electromagnetic wave emitted from the electromagnetic wave generator.

5. An image forming apparatus according to claim 4, wherein the spatial modulation unit is comprised of a material the dielectric constant of which varies according to an applied voltage; and
the dielectric constant spatially varies at the period equal to or shorter than the wavelength of the electromagnetic wave by controlling the applied voltage at an interval equal to or shorter than the wavelength of the electromagnetic wave.

6. An image forming apparatus according to claim 3, wherein the spatial signal intensity modulation to be applied consists of the modulations regarding two directions.

7. An image forming apparatus according to claim 1, wherein:
the signal processing section prepares in advance a spatial reference signal having a period equal to the period of the spatial signal intensity modulation applied to the electromagnetic wave which reaches the electromagnetic wave detecting unit is spatially modulated by the spatial modulation unit, and carries out a spatial synchronous detection using the measurement signal from the electromagnetic wave detecting unit and the spatial reference signal to extract from the measurement signal only a signal of a component corresponding to the period equal to the period of the spatial signal intensity modulation applied by the spatial modulation unit.

8. An image forming apparatus according to claim 1, wherein the electromagnetic wave comprises an electromagnetic wave including at least one frequency of a frequency region from 30 GHz to 30 THz.

9. An image forming method, comprising the steps of:
applying to an electromagnetic wave a spatial signal intensity modulation which includes at least one period component equal to or smaller than a wavelength of the electromagnetic wave to apply the spatial signal intensity modulation to an electromagnetic wave which reaches from an object to be measured which is to be irradiated with the electromagnetic wave to an electromagnetic wave detecting unit;
carrying out a spatial synchronous detection using a measurement signal derived from the electromagnetic wave which reaches the electromagnetic wave detecting unit and a spatial reference signal previously prepared and synchronized with the spatial signal intensity modulation to extract a signal of a component synchronized with the spatial signal intensity modulation from the measurement signal; and
image-processing the extracted signal to obtain an image of the object to be measured.

* * * * *